United States Patent
Gravekamp et al.

(10) Patent No.: US 10,398,792 B2
(45) Date of Patent: Sep. 3, 2019

(54) METHOD FOR PRODUCING RADIOBACTERIA FOR THERAPY OF CANCER

(71) Applicant: ALBERT EINSTEIN COLLEGE OF MEDICINE, Bronx, NY (US)

(72) Inventors: Claudia Gravekamp, New York, NY (US); Ekaterina Dadachova, Mahopac, NY (US); Dinesh Chandra, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 37 days.

(21) Appl. No.: 15/523,790

(22) PCT Filed: Oct. 19, 2015

(86) PCT No.: PCT/US2015/056190
§ 371 (c)(1),
(2) Date: May 2, 2017

(87) PCT Pub. No.: WO2016/073176
PCT Pub. Date: May 12, 2016

(65) Prior Publication Data
US 2017/0333578 A1   Nov. 23, 2017

Related U.S. Application Data (60) Provisional application No. 62/074,702, filed on Nov. 4, 2014.

(51) Int. Cl.
| | | |
|---|---|---|
| A61K 51/12 | (2006.01) |
| C12N 1/20 | (2006.01) |
| C09K 8/514 | (2006.01) |
| C09K 8/90 | (2006.01) |
| C12P 19/04 | (2006.01) |
| A61K 9/00 | (2006.01) |
| A61K 35/74 | (2015.01) |
| C12N 1/38 | (2006.01) |

(52) U.S. Cl.
CPC .......... *A61K 51/1203* (2013.01); *C09K 8/514* (2013.01); *C09K 8/90* (2013.01); *C12N 1/20* (2013.01); *C12P 19/04* (2013.01); *A61K 9/0019* (2013.01); *A61K 35/74* (2013.01); *C12N 1/38* (2013.01)

(58) Field of Classification Search
CPC .. A61K 51/1203; A61K 9/0019; A61K 35/74; C09K 8/90; C09K 8/514; C12P 19/04; C12N 1/20; C12N 1/38
See application file for complete search history.

(56) References Cited

U.S. PATENT DOCUMENTS

| 4,800,959 A | 1/1989 | Costerton et al. |
| 2014/0147379 A1 | 5/2014 | Dadachova et al. |

FOREIGN PATENT DOCUMENTS

WO   2012112317 A1   8/2012

OTHER PUBLICATIONS

PCT International Search Report and Written Opinion, dated Mar. 16, 2016 in connection with PCT International Application No. PCT/US2015/56190, 8 pages.

Robson J et al., entitled "Observations on the Labelling of a Strain of *Staphylococcus aureus* with Phosphorus-32," J. gen. Microbiol (1964), 36, 37-48.

*Primary Examiner* — Robert S Cabral
(74) *Attorney, Agent, or Firm* — Amster, Rothstein & Ebenstein LLP (57) ABSTRACT

A method of producing radiobacteria is provided, especially radiolisteria-$^{32}$P. Compositions and methods of use thereof are also provided.

15 Claims, 11 Drawing Sheets

METHOD FOR PRODUCING RADIOBACTERIA FOR THERAPY OF CANCER

CROSS-REFERENCE TO RELATED APPLICATIONS

This application is a U.S. national stage entry under 35 U.S.C. § 371 of PCT International Patent Application No. PCT/US2015/056190, filed Oct. 19, 2015, which claims benefit of U.S. Provisional Application No. 62/074,702, filed Nov. 4, 2014, the contents of each of which are incorporated herein by reference into the subject application.

BACKGROUND OF THE INVENTION

Throughout this application various publications are referred to by number in parentheses. Full citations for these references may be found at the end of the specification. The disclosures of these publications and of all books, patents and patent application publications cited herein, are hereby incorporated by reference in their entirety into the subject application to more fully describe the art to which the subject invention pertains.

Pancreatic ductal adenocarcinoma, synonymous to pancreatic cancer, is the 4th leading cause of cancer deaths. The "silent killer" is characterized by its metastatic behavior (3) before the primary tumor can be detected, resulting in a five-year survival rate of only 4%. Current cancer treatments, i.e. surgery, followed by radiation and/or chemotherapy, are ineffective against metastases. Gemcitabine and erlotinib, FDA-approved drugs for pancreatic cancer treatment, improve median survival by approximately six months in advanced stage patients (1-3), emphasizing the need for new alternative therapies for pancreatic cancer. One such approach could be *Listeria monocytogenes*-based cancer therapy.

This laboratory discovered that a highly attenuated *Listeria* (*Listeria$^{at}$*) provides a therapeutic approach that is particularly useful against metastatic cancer. Myeloid derived suppressor cells (MDSC) are normally a major problem in cancer vaccination because they strongly suppress T cell and natural killer (NK) cell responses and promote angiogenesis (4-10), resulting in the development of metastases. However, when infected with *Listeria$^{at}$* MDSC protect *Listeria$^{at}$* from immune clearance through their immune suppressive character (Chandra et al., unpublished results), and deliver *Listeria$^{at}$* safely to the tumor microenvironment where it infects and kills tumor cells through high levels of reactive oxygen species (ROS) (11). Also, *Listeria$^{at}$*-specific cytotoxic T lymphocytes (CTL) kills tumor cells, because infected tumor cells present *Listeria$^{at}$* antigens (11). Importantly, in normal tissues that lack immune suppression *Listeria$^{at}$* is rapidly cleared by macrophages, NK cells and CTL (11,12) which makes such treatment safe for human use.

Targeted radionuclide therapy has proven to be successful in treatment of several types of cancer and employs radiolabeled small molecules, monoclonal antibodies, peptides and other tumor-targeting vehicles (13). The radioactive particles emitted by the radionuclides physically destroy the cancerous cells and such therapies are not subject to multidrug resistance mechanisms. There have been attempts to utilize targeted radionuclide therapy in the form of radiolabeled tumor specific antibodies (Ab) (radioimmunotherapy) for treatment of pancreatic cancer. However, radioimmunotherapy of pancreatic cancer has shown very modest results both pre-clinically (14-16) and in cancer patients with unresectable liver metastases (17). New choices of targeting vehicles are needed to make targeted radionuclide therapy successful in treatment of pancreatic cancer.

Therapy with bacteria comprising radiolabelled antibodies has been demonstrated (e.g. see US Patent Application Publication No. 2014-0417379-A1, hereby incorporated by reference), but a simpler and more efficient and economical method for making radiobacteria is desirable.

The present invention addresses the need for new targeted cancer therapies by providing a simpler and more efficient and economical method for producing radiobacteria.

SUMMARY OF THE INVENTION

A method is provided for producing radiobacteria. In an embodiment, the method comprises obtaining a culture of bacteria, starving said bacteria for 5 to 60 minutes in a saline-based solution, and subsequently growing the bacteria in a radionuclide-containing medium for 5 to 240 minutes so as to produce radiobacteria.

Also provided is a method of treating a tumor in a subject, or reducing or preventing metastasis of a tumor in a subject, comprising administering to the subject an amount of radiobacteria produced by any of the methods disclosed herein effective to treat the tumor in the subject, or so as to reduce or prevent metastasis of the tumor in the subject.

BRIEF DESCRIPTION OF THE DRAWINGS

FIG. 3A-3B: Infection rate of tumor cells: Infection of 4T1 tumor cells with *Listeria*-$^{32}$P (LM-P32) was compared to *Listeria* untreated (LM) (A). The number of CFU per well after 1 hr of infection. This experiment was repeated several times as indicated at the x-axis. The error bars represents standard error of the mean (SEM). The infection rate was also tested with Panc-02 cells (B).

DETAILED DESCRIPTION OF THE INVENTION

Development of a protocol to incorporate $^{32}$P into attenuated Listeria monocytogenes for the treatment of cancer: It was found that Listeria-$^{32}$P developed with this protocol is highly effective against pancreatic cancer (80% of the mice are free of cancer after treatment with Listeria-$^{32}$P). This is significant, since pancreatic cancer is extremely difficult to treat. Herein an optimal incorporation protocol is disclosed involving, in one embodiment, first starving the Listeria monocytogenes in saline for 30 min, followed by growing the bacteria in phosphate-free medium added with $^{32}$P for 60 min, followed by a washing step, and then the Listeria-$^{32}$P is ready to inject. This is an extremely simple and cheap method to develop radioactive Listeria for the treatment of pancreatic (and other metastatic) cancers.

A method is provided for producing radiobacteria comprising obtaining a culture of bacteria, starving said bacteria for 5 to 60 minutes in a saline-based solution, and subsequently growing the bacteria in a radionuclide-containing medium for 5 to 240 minutes so as to produce radiobacteria.

In an embodiment, the radionuclide-containing medium in which the bacteria are grown a medium supplemented with $^{32}$P which is otherwise phosphate-free.

In an embodiment, the bacteria are attenuated. In an embodiment, the bacteria are Listeria monocytogenes. In an embodiment, the bacteria from which the radiobacteria are produced are any suitable gram-positive or gram-negative bacterium such as Salmonella thyphimurium, Vibrio cholera, Clostridium, or Bifidobacterium breve.

In an embodiment, the radionuclide is $^{32}$P.

In an embodiment, the bacteria are grown for 50-70 minutes in the radionuclide-containing medium. In an embodiment, the bacteria are grown for 60 minutes in the radionuclide-containing medium. In an embodiment, the method further comprises subsequently washing the radiobacteria and recovering them.

Also provided is a method of treating a tumor in a subject, or reducing or preventing metastasis of a tumor in a subject, comprising administering to the subject an amount of radiobacteria produced by any of the methods disclosed herein effective to treat the tumor in the subject, or so as to reduce or prevent metastasis of the tumor in the subject.

In an embodiment, the bacteria from which the radiobacteria are produced are Listeria monocytogenes. In an embodiment, the bacteria from which the radiobacteria are produced are any suitable gram-positive or gram-negative bacterium such as Salmonella thyphimurium, Vibrio cholera, Clostridium, or Bifidobacterium breve.

In an embodiment, the radiobacteria are administered systemically to the subject.

In an embodiment, the radiobacteria are administered locally to the tumor in the subject.

In an embodiment, the radiobacteria are injected into the tumor in the subject.

In an embodiment, the tumor is a pancreatic tumor.

In an embodiment, the tumor is a tumor of the ovary, uterus, neck, head, breast, prostate, liver, lung, kidney, neurones, glia, colon, testicle, or bladder or is a hepatocellular cancer.

In an embodiment, the tumor is an inoperable tumor. In an embodiment, the tumor is a late stage tumor. In an embodiment, the tumor is an established tumor. In an embodiment, the tumor is a stage III tumor. In an embodiment, the tumor is a stage IV tumor. In an embodiment, the tumor is not resectable.

In an embodiment, the amount of radiobacteria administered provides a radiation dose of 1-500 mCi. In an embodiment, the amount of radiobacteria administered provides a radiation dose of 1-5 mCi.

In an embodiment, the method is of treating a tumor in a subject.

In an embodiment, the method is of reducing or preventing metastasis of a tumor in a subject.

In a preferred embodiment, the bacteria of the inventions described herein are attenuated. An attenuated bacterium is one that has been treated so as to reduce its virulence compared to its wildtype state. For example, bacteria can be attenuated by silencing of genes in the genome of the bacteria or by genetic engineering of the bacteria. In a preferred embodiment, the bacteria of the inventions described herein are isolated or purified.

The invention is particularly useful for types of cancer for which there are practically no effective treatments, like pancreatic cancer (which is almost always detected in metastatic form), ovarian cancer, cancers for which surgery to remove the primary tumor is not an option because of tumor location (as is often the case in head and neck cancers), inoperable hepatocellular carcinoma, and for metastatic disease which is recurrent or refractory to the standard treatments (with non-limiting examples being lung and colon cancers as well as breast cancer).

In specific regard to using the radiobacteria disclosed herein to treat pancreatic cancer, intraperitoneal cavity administration is expected to be most optimal since the peritoneal cavity is filled with ascites containing MDSC. These MDSC will deliver the *Listeria*-32P to the tumor and metastases. Pancreatic cancer is most deadly because of the metastases.

As used herein, "treating" a tumor means that one or more symptoms of the disease, such as the tumor itself, metastasis thereof, vascularization of the tumor, or other parameters by which the disease is characterized, are reduced, ameliorated, prevented, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries.

As used herein, an "inoperable tumor" is as the term is commonly used in the art by medical practitioners. Inoperable tumors are generally those located in an inaccessible place (e.g. in a part of the brain mechanically inaccessible), or those that are composed of multiple tumors that cannot all be removed.

As used herein, reducing or preventing metastasis of a tumor means that any of the symptoms of the disease, such as the metastases, the extent of spread thereof, the vascularization of the metastases or other parameters by which the disease is characterized are reduced, ameliorated, prevented, placed in a state of remission, maintained in a state of remission, or eliminated.

"Radionuclide" as used herein means a radioisotope of an element. The choice of the particular radioisotope which the bacteria, such as *Listeria* comprises, will be determined by the type of tumor to be treated and its localization in the body. $^{32}$P is preferred. Two characteristics are important in the choice of a radioisotope—emission range in the tissue and half-life. In a preferred embodiment, the radioisotope is a beta emitter. Examples of beta emitters include 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131-Iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199-Gold (half-life 3.1 days). In a preferred embodiment, the beta-emitting radioisotope is the high-energy β-emitter 188-Rhenium ($E_{max}$=2.12 MeV). $^{188}$Re has the additional advantage that it emits γ-rays which can be used for imaging, for example to assess progress of treatment and successful localization of the radiobacteria, such as radiolisteria. Longer-lived isotopes such as 90-Yttrium (half-life 2.7 days), 177-Lutetium (half-life 6.7 days) or 131-Iodine (half-life 8 days) may also be used. Positron emitters, such as 68-Gallium (half-life 68 minutes), 18-Fluorine (half-life 110 minutes), and 61-Copper (half-life 3.4 hours), could also be used to treat abscesses, as well as disseminated diseases. In addition, radioisotopes which are Auger electron emitters and/or conversion electron emitters could be used; however, such radioisotopes need to be coupled to an antibody type which is internalized by the *Listeria*. Examples of Auger electron emitters include 67-Gallium (half-life 78 hours), 111-Indium (half-life 2.8 days), 123-Iodine (half-life 13 hours), 125-Iodine (half-life 60 days) and 201-Thallium (half life 3 days). Examples of conversion electron emitters include 117m-Tin (half-life 13.6 days). Examples of radioisotopes that emit both Auger electrons and conversion electrons include 195m-Mercury (half-life 41.6 hours) and 195m-Platinum (half-life 4 days). Such radioisotopes have needed to be coupled with anti-*Listeria* antibodies and then incubated with the *Listeria* bacteria, resulting in a stable binding between anti-*Listeria* antibody coupled with the isotopes, and the *Listeria* bacteria. The present invention is an improvement of this method.

Alpha emitters, which have a short emission range in comparison to beta emitters, may be preferable for treatment of tumors or cancers that are disseminated in the body or in the blood. Examples of alpha emitters include 213-Bismuth (half-life 46 minutes), 223-Radium (half-life 11.3 days), 224-Radium (half-life 3.7 days), 225-Radium (half-life 14.8 days), 225-Actinium (half-life 10 days), 212-Lead (half-life 10.6 hours), 212-Bismuth (half-life 60 minutes), 211-Astatin (half-life 7.2 hours), and 255-Fermium (half-life 20 hours). In a preferred embodiment, the alpha-emitting radioisotope is 213-Bismuth. $^{213}$Bi emits a high LET α-particle with E=5.9 MeV with a path length in tissue of 50-80 μm. Theoretically a cell can be killed with one or two α-particle hits. $^{213}$Bi is currently available in generator form, which allows transportation of this isotope from the source to clinical centers within the United States and abroad.

The dose of the radioisotope can vary depending on the localization of the tumor, the severity of the tumor, the method of administration of radiobacteria, such as radiolisteria, (local or systemic) and the decay scheme of the radioisotope. In order to calculate the doses which can significantly decrease or eliminate tumor without radiotoxicity to vital organs, a diagnostic scan of the patient with the radiobacteria, such as radiolisteria, with diagnostic radioisotope or with the low activity therapeutic radioisotope can be performed prior to therapy, as is customary in nuclear medicine. The dosimetry calculations can be performed using the data from the diagnostic scan.

Fractionated doses of radiobacteria, such as radiolisteria, can be used, or single doses, though the former may be preferable against tumors by being less radiotoxic to normal organs. Depending on the status of a patient and the effectiveness of the first treatment, the treatment may consist of one dose or several subsequent fractionated doses.

In one embodiment, the subject is a human, and the dose of the radioisotope delivered by way of radiobacteria, such as radiolisteria-$^{32}$P, is between 1-5 mCi. In different embodiments, the dose of the radioisotope delivered by way of radiobacteria, such as radiolisteria, is between 1-100 mCi, 101-200 mCi, 201-300 mCi, 301-400 mCi, or 401-500 mCi.

The radiobacteria, such as radiolisteria, therapy delivered herein can be administered over a period of time to the subject alone, or with an adjuvant, or in combination with another anti-cancer agent. In an embodiment, the anti-cancer agent is a chemotherapeutic.

Radiobacteria, such as radiolisteria, can be administered in any fashion known in the art for anti-tumor therapies. Any acceptable route of administration of the active compounds described herein can be used. For example, oral, lingual, sublingual, buccal, parenteral, intrabuccal, intrathecal, intracerebroventricular, intraperitoneal, intra-tumor or nasal administration can be effected without undue experimentation by means well known in the art.

For administration parenterally, such as, for example, by intravenous, intramuscular, intrathecal or subcutaneous injection, administration can be accomplished by incorporating the radiobacteria, such as radiolisteria, or a composition comprising such of the present invention into a solution or suspension. Such solutions or suspensions may also include sterile diluents such as water for injection, saline solution, fixed oils, polyethylene glycols, glycerine, propylene glycol or other synthetic solvents and other media with the proviso that they are compatible with radiobacteria, such as radiolisteria, viability. Buffers such as acetates, citrates or phosphates and agents for the adjustment of tonicity such as sodium chloride or dextrose may also be added to the extent they are compatible with radiobacteria, such as radiolisteria, viability. In non-limiting examples, the parenteral preparation can be enclosed in ampules, disposable syringes or multiple dose vials.

The radiobacteria, such as radiolisteria, may be associated with a pharmaceutically-acceptable carrier which is compatible with radiobacteria viability, thereby comprising a pharmaceutical composition. The pharmaceutical composition may comprise the radiobacteria in the pharmaceutically acceptable carrier. Alternatively, the pharmaceutical composition may consist essentially of the radiobacteria in a pharmaceutically acceptable carrier. Yet alternatively, the pharmaceutical composition may consist of the radiobacteria in a pharmaceutically acceptable carrier. The pharmaceutically-acceptable carrier must be compatible with the radiobacteria, and not unduly deleterious to the subject. The choice of carriers will depend on the method of administration.

The subject can be a mammal. In different embodiments, the mammal is a mouse, a rat, a cat, a dog, a horse, a sheep, a cow, a steer, a bull, livestock, a primate, a monkey, or preferably a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Herein is disclosed a protocol for the incorporation of $^{32}$P into attenuated *Listeria monocytogenes*. The attenuated *Listeria*, into which the $^{32}$P is incorporated by the protocols disclosed herein, has been tested in human clinical trials (Maciag et al, 2009, Vaccine 27: 3975-3983). The protocol development involved analyzing the following criteria: incorporation efficiency of $^{32}$P into *Listeria*, viability of *Listeria*-$^{32}$P compared to *Listeria* alone, infection rate of tumor cells of *Listeria*-$^{32}$P compared to *Listeria* alone, incorporation of $^{32}$P into normal tissues, toxicity of *Listeria*-$^{32}$P, efficacy of *Listeria*-$^{32}$P in pancreatic model (Panc-02 model), and penetration of *Listeria* into pancreatic tumor in KPC model.

Figure 1:
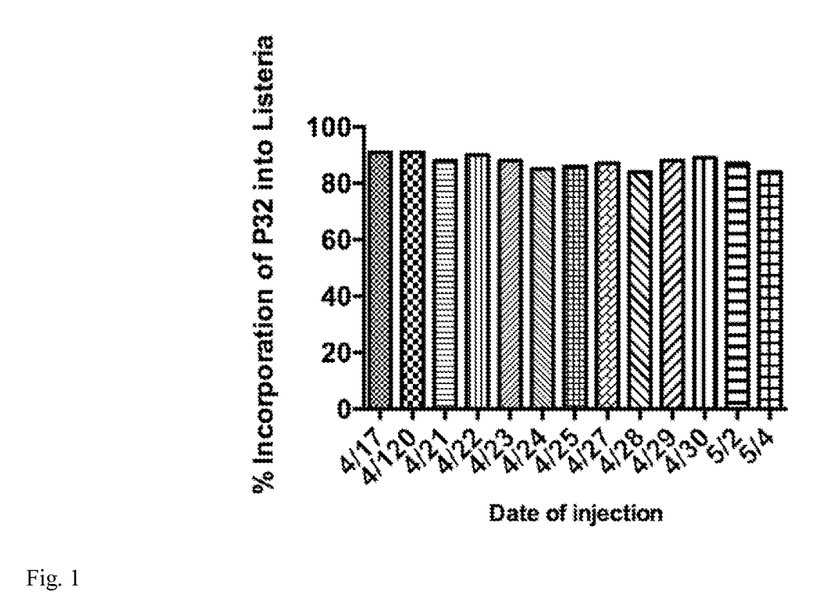
FIG. 1: Incorporation of $^{32}$P into *Listeria*: *Listeria* bacteria were starved in saline for 30 min, followed by culturing in phosphate-free medium (Edinburgh Minimal Medium Phosphate free) for 1 hr, then washed and resuspended in saline for injection ($10^7$/200 μl). This experiment was repeated as indicated at the x-axis for reproducibility.

Incorporation of $^{32}$P into *Listeria*: For the incorporation of $^{32}$P into the *Listeria*, the bacteria were first starved in saline, and then cultured in phosphate-free medium complemented with $^{32}$P. Various starvation times (30, 60, 120 min.), incorporation times (30, 60, 120 min.), and amounts of $^{32}$P (10, 50, 100, 300 µCi) were tested. Using 30 min. of starvation in saline, followed by 60 min. culture into phosphate-free yeast medium was found to produce the best results with $0.5 \times 10^9$ CFU of *Listeria* and 50 µCi of $^{32}$P. Using this protocol, 93% of all the $^{32}$P was incorporated into the *Listeria* with high reproducibility (FIG. 1).

Figure 2:
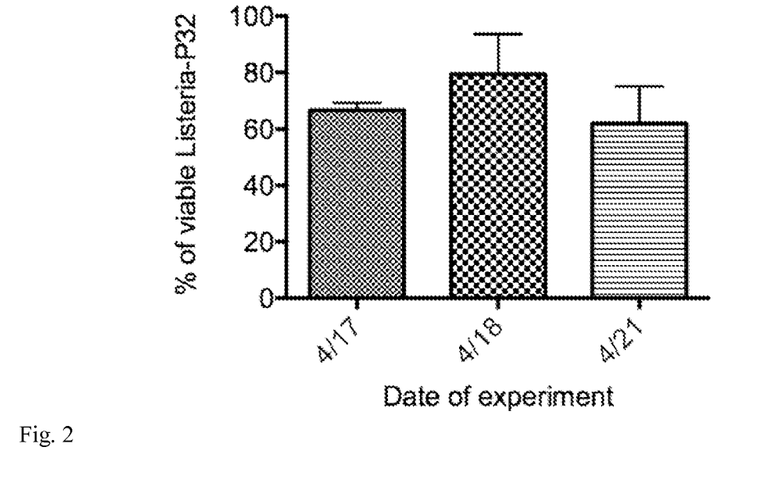
FIG. 2: Viability of *Listeria*-$^{32}$P: After incorporation of $^{32}$P into *Listeria* the viability of *Listeria* was compared to *Listeria* untreated (Viability *Listeria*-$^{32}$P/Viability *Listeria* untreated×100%). This experiments was repeated several times as indicated at the x-axis. The error bars represents standard error of the mean (SEM).

Viability of *Listeria*-$^{32}$P: During the development of incorporation of $^{32}$P into *Listeria*, it was experimentally tested whether the $^{32}$P affected the viability of the *Listeria* (Quispe-Tintaya et al., 2013b). For this purpose, serial dilutions of untreated *Listeria* and *Listeria* incorporated with $^{32}$P were made on agar plates and the number of live CFU of *Listeria* of both were determined next day (FIG. 2).

Figure 3A:
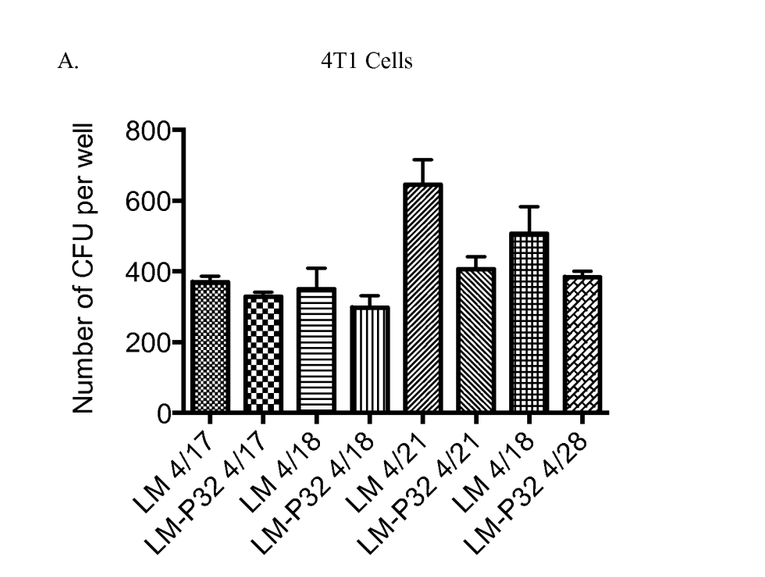
Figure 3B:
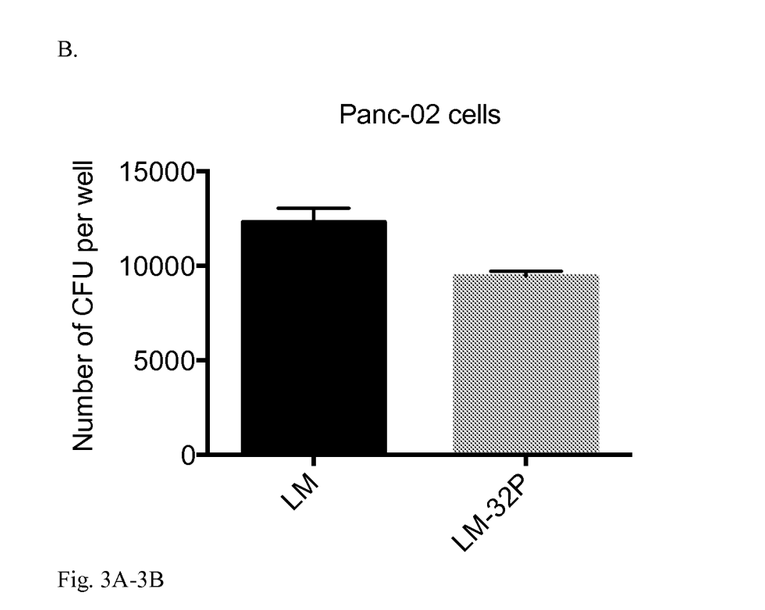

Infection rate of *Listeria*-$^{32}$P: Also the infection rate of tumor cells with *Listeria*-32P was determined by culturing tumor cells with *Listeria* or *Listeria*-$^{32}$P for 2 hrs, and then lysed in water and plated on agar as described previously (Quispe-Tintaya et al., 2013b). The number of live CFU of *Listeria* was determined next day (FIG. 3).

Figure 4:
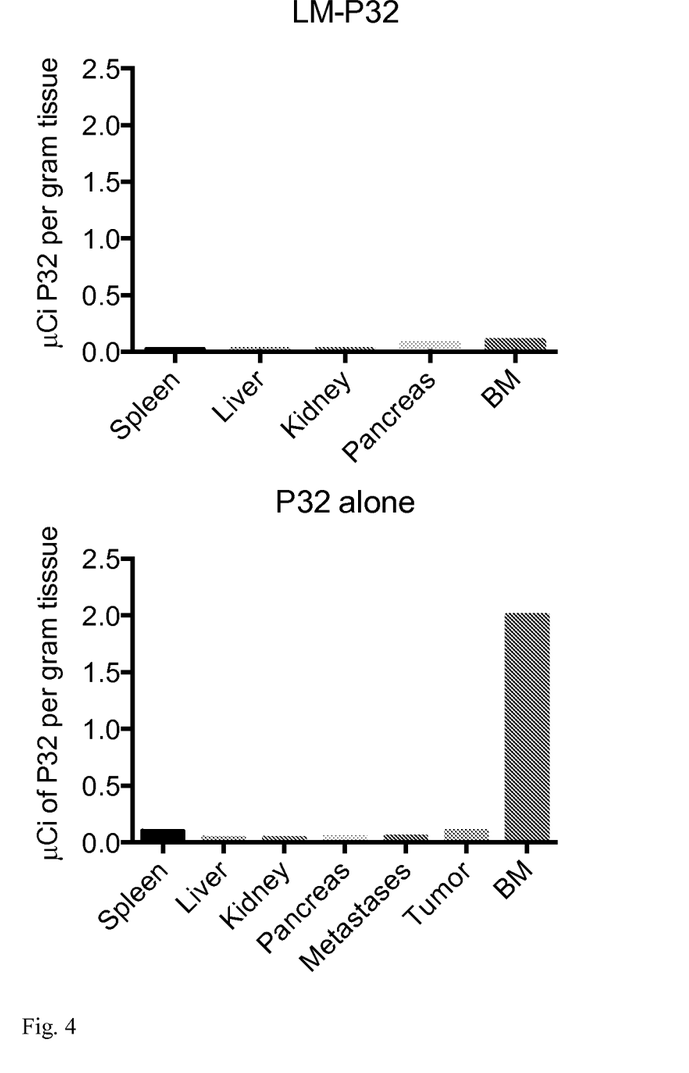
FIG. 4: Incorporation of radioactive counts into normal tissues: At the end of treatment with *Listeria*-$^{32}$P, mice were euthanized and tissues were analyzed for radioactive counts using a scintillation counter, and normalized for μCi using a standard curve with known amounts (μCi) of $^{32}$P. $P^{32}$ alone strongly incorporated into bone marrow (BM) cells, but not $^{32}$P incorporated into the *Listeria*.

Incorporation of $^{32}$P into normal tissue: The biodistribution of $^{32}$P delivered through *Listeria* or $^{32}$P as a single compound in mice with pancreatic cancer were both analyzed at the end of the treatment. It was determined that the levels of $^{32}$P incorporated into bone marrow (BM) were significantly higher after treatment with $^{32}$P alone compared to *Listeria*-$^{32}$P (FIG. 4). This is an important result from safety point of view.

Toxicity of *Listeria*-$^{32}$P: The effect of *Listeria* $^{32}$P was analyzed on liver, kidney, bone marrow, bone and small intestine by pathological examination directly after the treatments, and one month after the treatments with *Listeria*-$^{32}$P compared to the saline mice. It was found in some inflammatory cells in mice directly after treatment with *Listeria*-$^{32}$P, but this was not significantly different from mice without treatment, which is consistent with the low incorporation levels in normal tissues when treated with *Listeria*-$^{32}$P. Also, the BM cellularity of the mice treated with *Listeria*-$^{32}$P was slightly greater than in the saline mice. However, one month after treatment no effect of the *Listeria*-$^{32}$P was observed on normal tissues.

Figure 5:
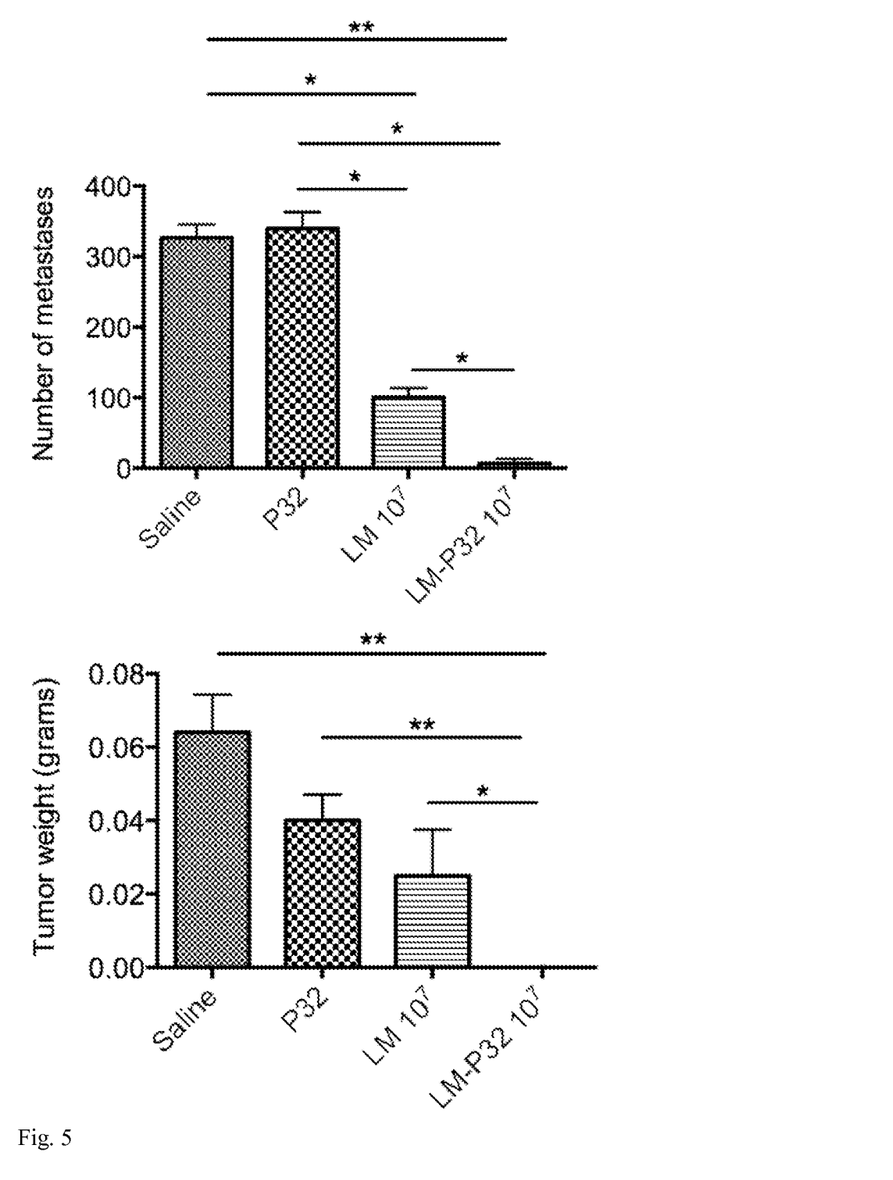
FIG. 5: Efficacy study of *Listeria*-$^{32}$P in Panc-02 model: C57Bl6 mice received 2×10$^6$ Panc-02 tumor cells into the mammary fat pad, and three days later the mice were treated with *Listeria*-$^{32}$P ($10^7$ CFU) every three days (ip) until day 20. All mice were euthanized on day 21 and analyzed for number of metastases and tumor weight. All untreated mice developed a small primary tumor in the mammary fat, metastases in liver and other organs, and ascites in the peritoneal cavity within 21 days. N=5 mice per group. Representative of 2 experiments. 4 out of 5 mice were free of cancer. Mann-Whitney *p<0.05, **p<0.01. Metastases are found particularly in the liver.

Efficacy of *Listeria*-$^{32}$P in mouse model of pancreatic cancer: Finally, after demonstrating that the viability and function of *Listeria* was not altered by $^{32}$P, and that safety aspects were highly encouraging, the efficacy of *Listeria*-$^{32}$P was determined in mice with pancreatic cancer (Panc-02 model). For this purpose, mice were challenged with Panc-02 tumor cells (mammary fat pad) on day 0, and treated with $10^7$ CFU of *Listeria*-$^{32}$P every three days (ip) as described for *Listeria*-188Re (Quispe-Tintaya et al., 2013b). It was found that 80% of the mice were free of cancer (FIG. 5).

Figure 6:
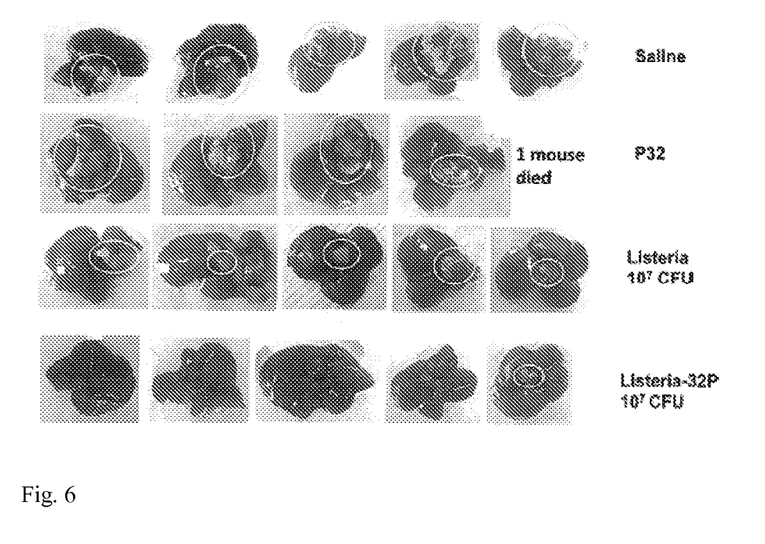
FIG. 6: Listeria-$^{32}$P nearly completely eliminates liver metastases in Panc-2 model.

Since pancreatic cancer metastasizes particularly to the liver, an example of elimination of metastases in the liver of the Panc-02 model by *Listeria*-$^{32}$P (FIG. 6), shows the effectiveness of this method in treating metastasis also.

Figure 7:
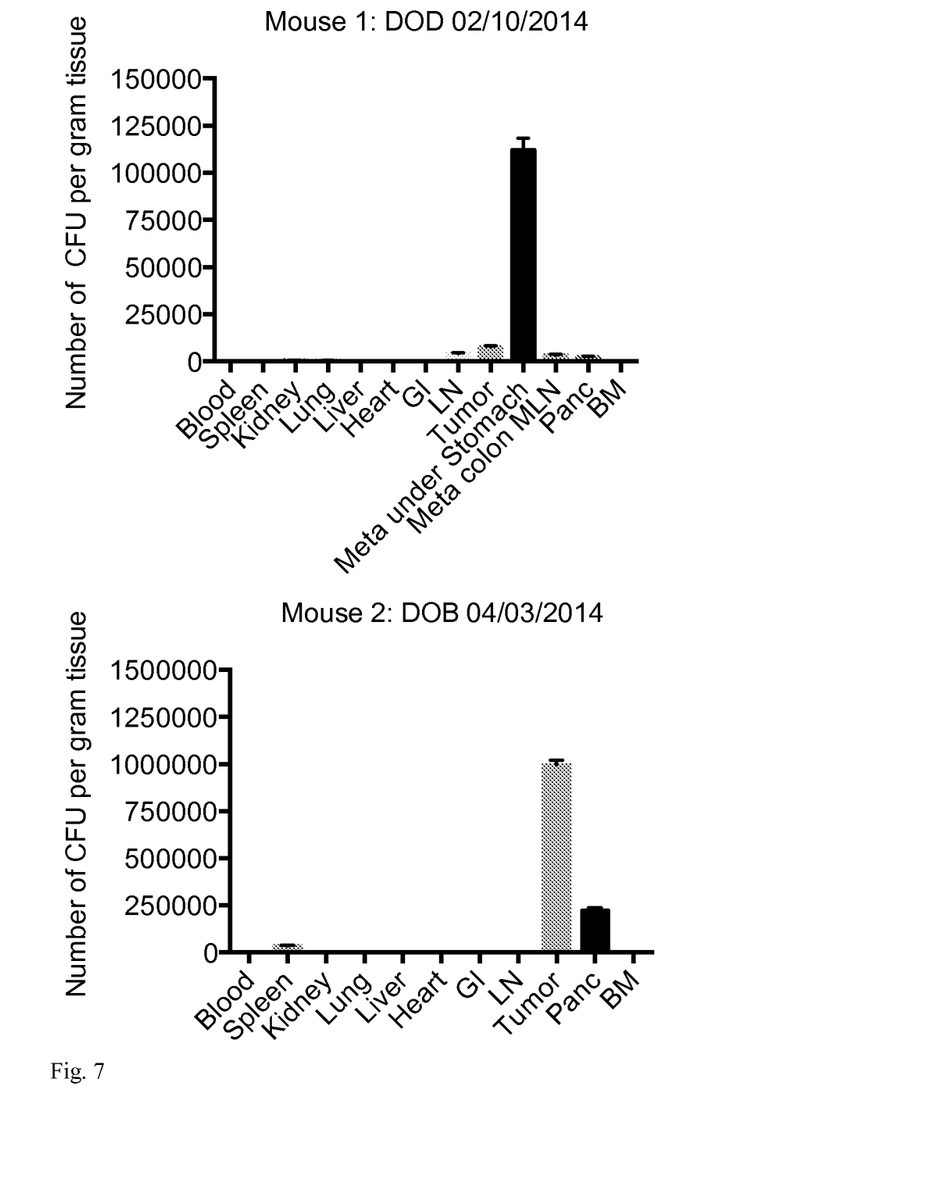
FIG. 7: Penetration of Listeria into pancreatic tumors, metastases and normal tissues. KPC mice of 6 and 4 month old with a pancreatic tumor (and metastases in one of the two mice) were injected with $10^7$ CFU of Listeria and the next day analyzed for the number of CFU of Listeria bacteria. Tissues were macerated between frosted object slides, lysed in water, and plated on agar. Listeria bacteria were predominantly found in the tumors and metastases, and in the pancreas (pancreas tissue could not be separated from pancreatic tumor macroscopically). Note that zero bacteria were found in the bone marrow.

Penetration of *Listeria* into the pancreatic tumor in the KPC model: In cancer patients the stromal barrier prevents the tumor from uptake of drugs (Olive et al., 2009). Herein it is demonstrated that *Listeria* do penetrate the pancreatic tumors and metastases of the KPC model. KPC mice were injected with $10^7$ CFU of *Listeria* ip, and next day CFU were isolated from normal tissues, tumors and metastases. Similar to the 4T1 and Panc-02 model, *Listeria* bacteria were abundantly found in the metastases and tumors of the KPC model and much less or not in normal tissues (FIG. 7).

Figure 8:
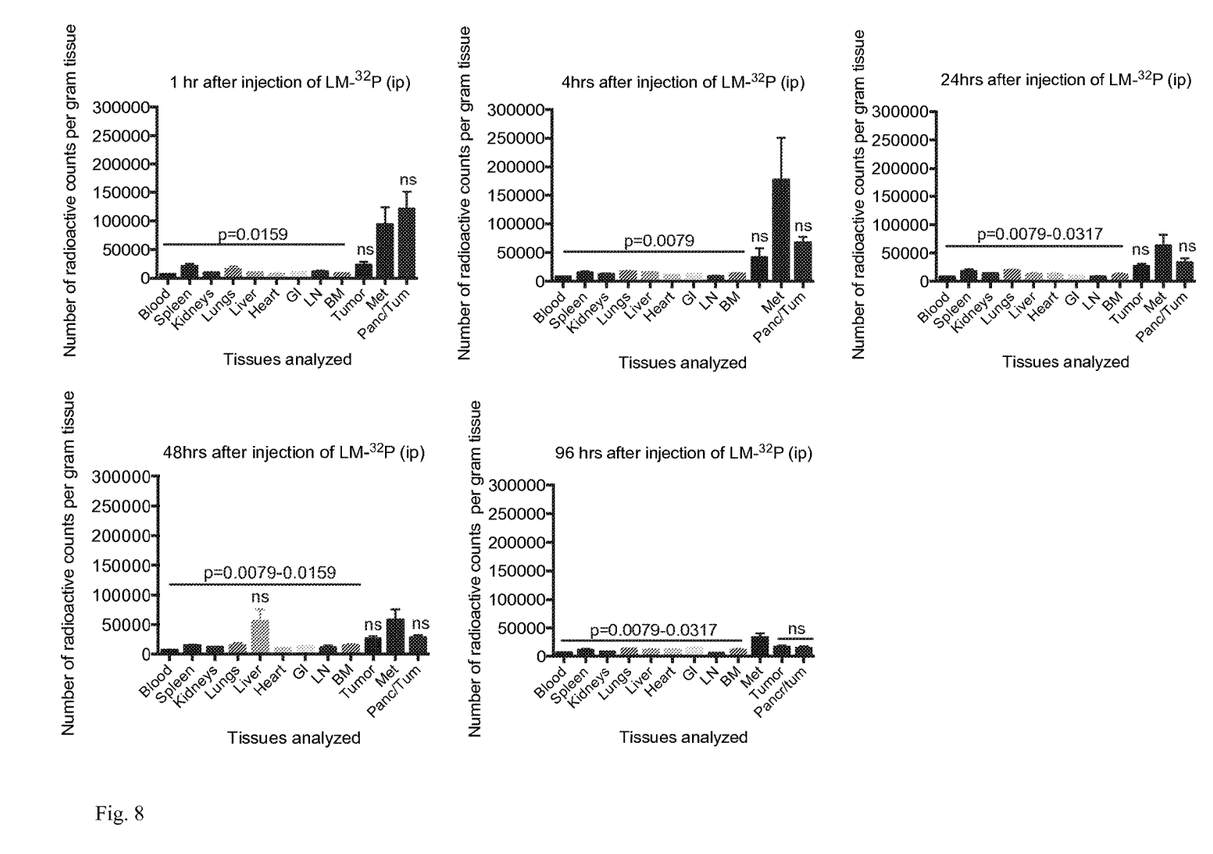
FIG. 8: Biodistribution of $^{32}$P-Mice with Panc-02 tumors and metastases were injected once with $10^7$ Listeria-$^{32}$P and analyzed for the number of radioactive counts in primary tumor, metastases, and in various normal tissues at various time intervals (1, 4, 24, 48, and 96 hrs). As shown here, $^{32}$P was highest in metastases and tumors, particularly at 1 and 4 hrs after the injection while at 24, 48, and 96 hrs after the injection the $^{32}$P levels decreased but stayed significantly higher compared to the normal tissues. An exception was found for the liver, because metastases already spread to this organ.

Further confirming experiments are shown in FIGS. 8-11. In FIG. 8, biodistribution of $^{32}$P was determined in mice with Panc-02 tumors and metastases. The mice were injected once with $10^7$ *Listeria*-$^{32}$P and analyzed for the number of radioactive counts in primary tumor, metastases, and in various normal tissues at various time intervals (1, 4, 24, 48, and 96 hrs). As shown, $^{32}$P was highest in metastases and tumors, particularly at 1 and 4 hrs after the injection while at 24, 48, and 96 hrs after the injection the $^{32}$P levels decreased but stayed significantly higher compared to the normal tissues. An exception was found for the liver, because metastases already spread to this organ.

Figure 9:
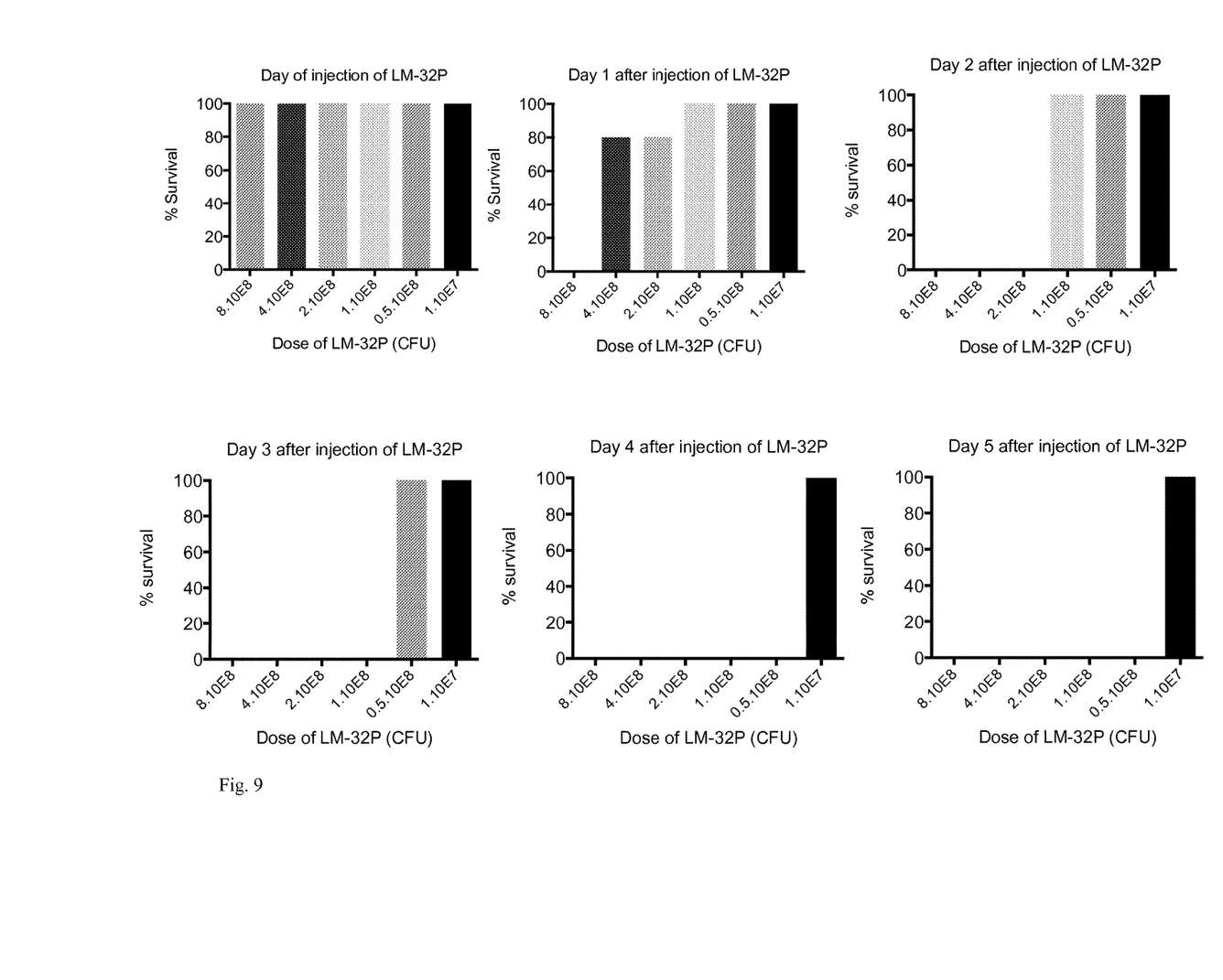
FIG. 9: Dose limiting toxicity (DLT) study—Various doses of Listeria-$^{32}$P were injected in C57Bl6 mice without cancer and the survival time was determined over the next 5 days. As shown here, $10^7$ CFU was the optimal dose, while $10^8$ CFU mice resulted in deaths on day 1 and thereafter, which is consistent with the $LD_{50}=10^8$ published for Listeria alone. These results indicate that the dose of $10^7$ CFU delivering 1 µCi of radioactivity per dose is non-toxic. This is also supported by the pathology reports which demonstrated no side effects, even in mice that received 12 doses of $10^7$ CFU of Listeria-$^{32}$P.

A dose limiting toxicity (DLT) study was performed (see FIG. 9). Various doses of *Listeria*-$^{32}$P were injected in C57Bl6 mice without cancer and the survival time was determined over the next 5 days. As shown, $10^7$ CFU was the optimal dose, while $10^8$ CFU mice resulted in deaths on day 1 and thereafter, which is consistent with the $LD_{50}=10^8$ published for *Listeria* alone. These results indicate that the dose of $10^7$ CFU delivering 1 µCi of radioactivity per dose is non-toxic. This is also supported by the pathology reports which demonstrated no side effects, even in mice that received 12 doses of $10^7$ CFU of *Listeria*-$^{32}$P.

Figure 10:
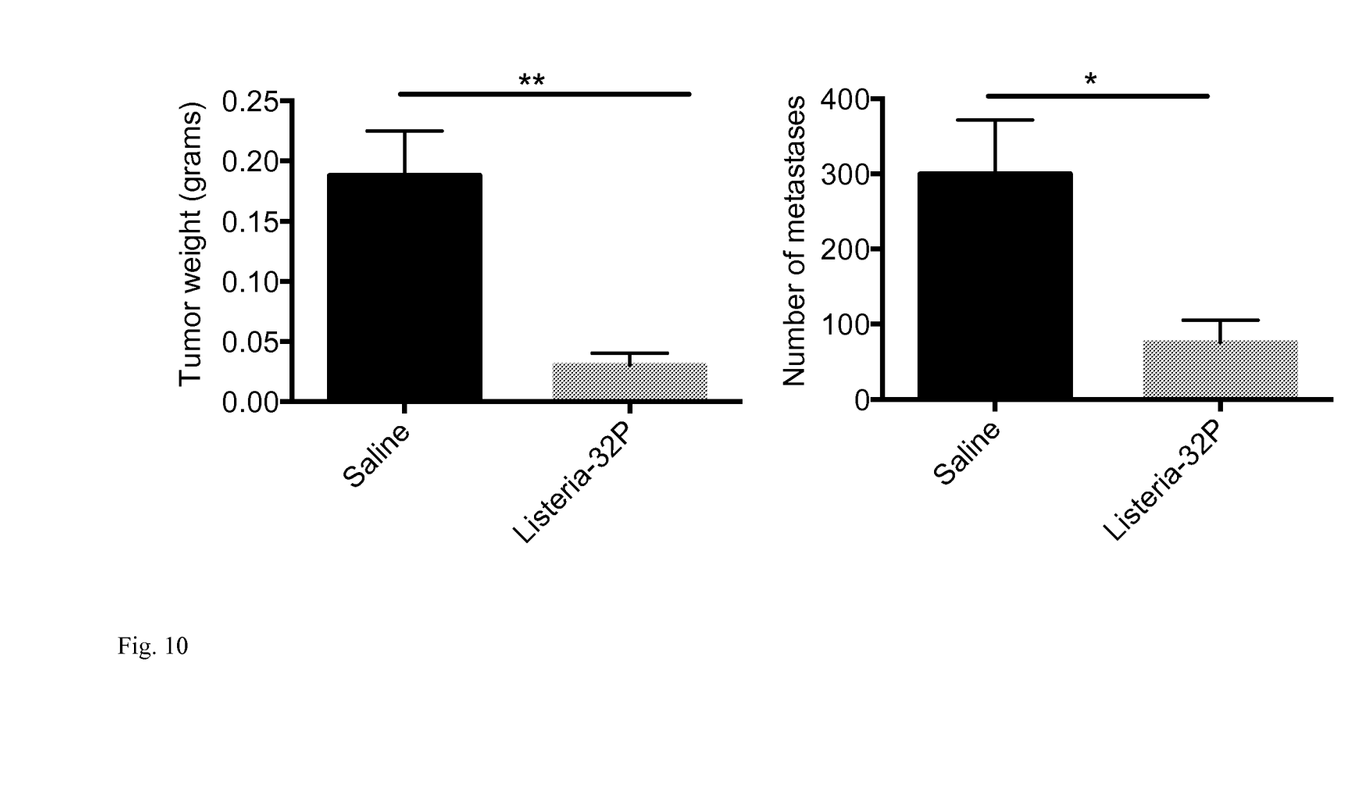
FIG. 10: The effect of Listeria-$^{32}$P on established tumors and metastases—A study was performed with Listeria-$^{32}$P and Saline on established tumors (0.5-1 cm) and metastases. Briefly, three cycles of $10^7$ CFU of Listeria-$^{32}$P were administered on four consecutive days, followed by a rest period of three days between each cycle (12 doses total). In contrast to previous experiments, the first treatment was started on day 10 instead of day 3. As shown here, the Listeria-$^{32}$P treatment strongly eradicated both tumors and metastases. ANOVA *p<0.05, **p<0.005 is significant.

The effect of *Listeria*-$^{32}$P on established tumors and metastases was performed with *Listeria*-$^{32}$P and Saline on established tumors (0.5-1 cm) and metastases (see FIG. 10). Briefly, three cycles of $10^7$ CFU of *Listeria*-$^{32}$P were administered on four consecutive days, followed by a rest period of three days between each cycle (12 doses total). In contrast to previous experiments, the first treatment was started on day 10 instead of day 3. As shown here, the *Listeria*-$^{32}$P treatment strongly eradicated both tumors and metastases. ANOVA *p<0.05, **p<0.005 is significant.

Figure 11:
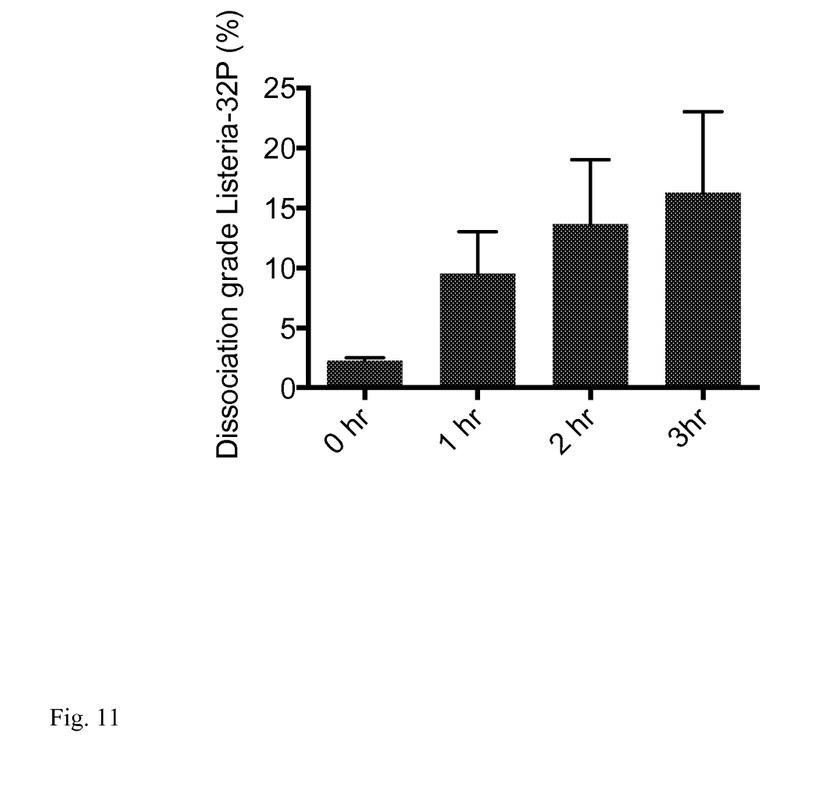
FIG. 11: Dissociation grade of Listeria-$^{32}$P in serum—The stability of Listeria-$^{32}$P in serum was analyzed by incubating Listeria-$^{32}$P with serum at 37° C. After 0, 1, 2 and 3 h, the RL bacteria were centrifuged, and the supernatant was analyzed for radioactive counts. The dissociation grade (percent) of the Listeria-$^{32}$P complex was determined by dividing free radioactivity in the supernatant with the radioactivity in the pelleted bacteria×100%. Data shown are the average of two experiments. The error bars represent SEM.

The dissociation grade of *Listeria*-$^{32}$P in serum was analyzed by incubating *Listeria*-$^{32}$P with serum at 37° C. After 0, 1, 2 and 3 h, the RL bacteria were centrifuged, and the supernatant was analyzed for radioactive counts. The dissociation grade (percent) of the *Listeria*-$^{32}$P complex was determined by dividing free radioactivity in the supernatant with the radioactivity in the pelleted bacteria×100%. Data shown in FIG. 11 are the average of two experiments. The error bars represent SEM.

Materials and Methods
Exemplary Protocol for Incorporation of $^{32}$P into *Listeria*
  Starvation of *Listeria*
    Take out a frozen tube of attenuated *Listeria monocytogenes* (LM) from −80° C. and thaw it in a 37° C. water bath (tube contains 1.5 mls): perform in duplex because 1 tube for LM-P32 and one tube for LM alone. Make $0.5×10^9$ bact/ml as follows.
    Vortex for 10 seconds and transfer 1 ml to a new tube;
    Centrifuge the 1 ml at 15000 rpm for 120 seconds;
    Discard the supernatant and wash the bacteria with 1 ml of saline;
    Centrifuge the 1 ml at 15000 rpm for 120 seconds;
    Discard the supernatant and resuspend the pellet in saline (if $0.8×10^9$ bact in pellet then resuspend in 0.8 mls saline→$10^9$/ml); then make the concentration of bacteria $0.5×10^9$ by adding 500 µl of saline to 500 µl of the bacteria; and
    Transfer the 1 ml of bacteria ($0.5×10^{e9}$) in saline from the eppendorf into a 15 ml tube;
    Close the 15 ml tube and starve the bacteria in saline for 30 minutes in 37° C. on shaker (200 rpm).
  Incorporation of the $^{32}$P into *Listeria* (RL)
    After the 30 min of starvation vortex the 15 ml tube and transfer the 1 ml into an eppendorf tube and centrifuge the tube at 15000 rpm for 120 seconds;
    Discard the supernatant and resuspend the pellet in 1 ml of phosphate free medium (EMMP) and vortex it well;
    Transfer 1 ml of bacteria solution from the eppendorf tube into a 15 ml tube again and add 5 ul of 10 uCi/ul $^{32}$P (add 50 µCi to $0.5×10^{e9}$/1 ml phosphate-free medium); and
    Close the 15 ml tube and incubate the bacteria for 60 minutes in 37° C. on shaker for $^{32}$P incorporation (200 rpm).
  Preparing for Measuring Radioactivity in Supernatant and Bacteria
    After 60 minutes of incubation transfer the $0.5×10^{e9}$ RL/1 ml culture again into an eppendorf tube and centrifuge the tube at 15000 rpm for 120 seconds;
    Take out 100 ul of supernatant and save it for measuring the non-incorporated $^{32}$P and discard rest of supernatant;
    Resuspend the pellet in 1 ml of saline vortex it nicely and centrifuge the tube at 15000 rpm for 120 seconds;
    Discard the supernatant and resuspend the pellet in 500 ul saline (to make the final dilution of bacteria $10^{e9}$/ml. Vortex it well and make sure the pellet is completely resuspended; and
    Take 100 µl out of 500 µl with $10^{e9}$ RL/1 ml to save it for measuring $^{32}$P incorporation (make sure to divide the radioactive counts by 2 in order to be equal with the supernatant).
  Viability of RL
    Use another 100 µl ($10^{e9}$/ml; dilute $10^{e5}$×) for plating the bacteria on LB after dilution to $10^{e4}$CFU/ml (plate 100 µl of $10^{e4}$/ml on each LB plate).
  Injection of RL into Mice
    For injecting into mice make a final dilution of $5×10^{e7}$ CFU of LM-P32/ml saline and inject 200 µl in each mice [100 µl of $0.5×10^9$ *Listeria*-P32/ml plus the 900 µl saline→inject 200 µl ip]. Make sure to make double and also do for LM alone the same.
  Infection Rate of Tumor Cells by RL
    For testing infection rate add 100 µl with $10^{e8}$ CFU of p32 incorporated bacteria to 4T1 cells plated on 24-well plate ($10^{e6}$ cells/well in 500 µl of DMEM with 10% FBS without antibiotics). Infect cells for 2 hrs. and add gentamicine 50 µg/ml final concentration for 1 h. After 1 h. take out the media completely and wash the infected cell one time with 1 ml warm media without any antibiotics. Finally lyse the cells using 1 ml of water for 5 minutes. Mix the lysate nicely by pipetting the lysed cells up and down for 20× and then transfer the lysate into Eppendorf tube. Vortex nicely and plate 100 µl on LB plate.
  Incorporation Medium
    US Biologicals Life Sciences Edinburgh Minimal Media Phosphate Free (EMMP) powder—Catalog: E2205-20
    Dissolve 29.328 grams per liter $H_2O$. Adjust pH to 5.5;
    Autoclave or filter sterilize (0.2 µm);
    Store at RT.

REFERENCES

1. A. Maitra, and R. H. Hruban, "Pancreatic cancer." *Annu. Rev. Pathol.* 3, 157-188 (2008).
2. M. J. Moore, D. Goldstein, J. Hamm, A. Figer, J. R. Hecht, S. Gallinger, H. J. Au et al, Erlotinib plus gemcitabine compared with gemcitabine alone in patients with advanced pancreatic cancer: A Phase III trial of the National Cancer Institute of Canada Clinical Trials Group. *J Clin Oncol* 15, 1960-1966 (2007).
3. M. H. Kulke, L. S. Blaszkowski, D. P. Ryan, J. W. Clark, et al, Capecitabine plus Erlotinib in Gemcitabine-refractory advanced pancreatic cancer. *J. Clin. Oncol.* 25, 4787-4792 (2007).
4. D. I. Gabrilovich, and S. Nagaraj, Myeloid-derived suppressor cells as regulators of the immune system. *Nat. Rev. Immunol.* 9, 162-174 (2009).
5. S. Ostrand-Rosenberg, and P. Sinha, Myeloid-derived suppressor cells: Linking inflammation and Cancer. *J. Immunol.* 182, 4499-4506 (2009).
6. P. Serafini, and V. Bronte. Myeloid-derived suppressor cells in cancer. In: Tumorinduced Immune Suppression. Eds Gabrilovich DI and Hurwitz AA. Springer. Pp157-194 (2008).
7. A. Mantovani, A. Sica, and M. Locati M. New vistas and macrophage differentiation and activation. *Eur. J. Immunol.* 37, 14-16 (2007).
8. P. Sinha, V. K. Clements, and S. Ostrand-Rosenberg, Interleukin-13-regulated M2 macrophages in combination with myeloid suppressor cells block immune surveillance against metastases. *Cancer Res.* 65, 11743-11751 (2005).
9. C. Murdoch, M. Muthana, S. B. Coffelt, and C. E. Lewis, The role of myeloid cells in the promotion of tumor angiogenesis. *Nature Reviews Cancer* 8, 618-631 (2008).
10. M. C. Schmid, and J. A. Varner, Myeloid cells in the tumor microenvironment: Modulation of tumor angiogenesis and tumor inflammation. *J. Oncol.* doi: 10.1155/2010/201026 (2010).
11. S. H. Kim, F. Castro, Y. Paterson, C. Gravekamp, High efficacy of a *Listeria*-based vaccine against metastatic breast cancer reveals a dual mode of action. *Cancer Res.* 69, 5860-5866 (2009).
12. E. Muraille, E. Narni-Mancinelli, P. Gounon, D. Bassand, N. Glaichenhaus, L. L. Lenz, G. Lauvau, Cytosolyc expression of SecA2 is a preruiquisite for long-term protective immunity. *Cell. Microbiol.* Doi: 10.1111/j.1462-5822.2007.00883.x (2007).
13. Targeted Radionuclide Therapy. Ed. Tod Speer, Lippincott, Williams & Wilkins, Philadelphia (2010).
14. L. Bodel, M. Cremonesi, C. Grana, P. Rocca, M. Bartelomei, M. Chinol, G. and Paganelli, Receptor radionuclide therapy with 90Y-[DOTA]0-Tyr3-octreotide (90YDOTATOC) in neuroendocrine tumors. *Eur. J. Med. And Mol. Imaging* 31, 1038-1046, 2004.
15. D. E. Milenic, K. Garmestani, E. D. Brady, P. S. Albert, D. Ma, A. Abdulla, M. W. Brechbiel, Alpha-particle radioimmunotherapy of disseminated peritoneal disease using a (212) Pb-labeled radio-immunoconjugate targeting HER2. *Cancer Biother Radiopharm,* 20, 557-68 (2005).
16. D. V. Gold, Z. Karanjawala, D. E. Modrak, D. M. Goldenberg, R. H. Hruban, PAM4-reactive MUC1 is a biomarker for early pancreatic adenocarcinoma. *Clin. Cancer Res.* 13, 7380-7 (2007).
17. A. Sultana, S. Shore, M. G. Raraty, S. Vinjamuri, J. E. Evans, C. T. Smith, S. Lane, S. Chauhan, L. Bosonnet, C. Garvey, R. Sutton, J. P. Neoptolemos, P. Ghaneh, Randomised Phase I/II trial assessing the safety and efficacy of radiolabelled anticarcinoembryonic antigen I(131) KAb201 antibodies given intra-arterially or intravenously in patients with unresectable pancreatic adenocarcinoma. *BMC Cancer* 25, 966-971 (2009).

The invention claimed is:

1. A method for producing radiobacteria comprising obtaining a culture of attenuated *Listeria monocytogenes* bacteria, starving said bacteria for 5 to 60 minutes in a saline-based phosphate-free solution, and subsequently growing the bacteria in is a radionuclide-containing medium supplemented with $^{32}P$ which is otherwise phosphate-free for 50-70 minutes so as to produce radiobacteria.

2. The method of claim 1, wherein the bacteria are grown for 60 minutes in the radionuclide-containing medium.

3. The method of claim 1, further comprising subsequently washing the radiobacteria and recovering them.

4. A method for treating a tumor in a subject, or for reducing or preventing metastasis of a tumor in a subject, comprising administering to the subject an amount of radiobacteria produced by the method of claim 1 effective to treat the tumor in the subject, or so as to reduce or prevent metastasis of the tumor in the subject.

5. The method claim 4, wherein the bacteria from which the radiobacteria are produced are *Listeria monocytogenes*.

6. The method of claim 4, wherein the radiobacteria are administered systemically to the subject.

7. The method of claim 4, wherein the radiobacteria are administered locally to the tumor in the subject.

8. The method of claim 7, wherein the radiobacteria are injected into the tumor in the subject.

9. The method of claim 4, wherein the tumor is a pancreatic tumor.

10. The method of claim 4, wherein the tumor is a tumor of the ovary, uterus, neck, head, breast, prostate, liver, lung, kidney, neurones, glia, colon, testicle, or bladder or is a hepatocellular cancer.

11. The method of claim 4, wherein the tumor is an inoperable tumor.

12. The method of claim 4, wherein the amount of radiobacteria administered provides a radiation dose of 1-500 mCi.

13. The method of claim 4, wherein the amount of radiobacteria administered provides a radiation dose of 1-5 mCi.

14. The method of claim 4, wherein the method is for treating a tumor in a subject.

15. The method of claim 4, wherein the method is for reducing or preventing metastasis of a tumor in a subject.

* * * * *